(12) United States Patent
Brown

(10) Patent No.: US 7,317,942 B2
(45) Date of Patent: Jan. 8, 2008

(54) DYNAMIC DISCRIMINATION UTILIZING ANTI-TACHY PACING THERAPY IN AN IMPLANTABLE MEDICAL DEVICE

(75) Inventor: Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 10/839,634

(22) Filed: May 5, 2004

(65) Prior Publication Data

US 2005/0251217 A1    Nov. 10, 2005

(51) Int. Cl.
   *A61N 1/362* (2006.01)
(52) U.S. Cl. .................. 607/14; 607/4; 607/9; 607/15
(58) Field of Classification Search ............ 607/4, 607/9, 14, 15
   See application file for complete search history.

(56) References Cited

U.S. PATENT DOCUMENTS

| 4,407,288 | A | 10/1983 | Langer et al. ........ 128/419 PG |
| 4,428,378 | A | 1/1984 | Anderson et al. ..... 128/419 PG |
| 4,821,723 | A | 4/1989 | Baker, Jr. et al. ....... 128/419 D |
| 4,865,036 | A | 9/1989 | Chirife ................... 128/419 D |
| 4,967,747 | A | 11/1990 | Carroll et al. .......... 128/419 D |
| 5,176,137 | A | 1/1993 | Erickson et al. ........ 128/419 D |
| 5,209,229 | A | 5/1993 | Gilli ....................... 128/419 D |
| 5,251,624 | A | 10/1993 | Bocek et al. ................... 607/6 |
| 5,330,505 | A | 7/1994 | Cohen ........................... 607/6 |
| 5,662,688 | A | 9/1997 | Haefner et al. ................ 607/5 |
| 5,855,593 | A | 1/1999 | Olson et al. ................... 607/9 |
| 2003/0023273 | A1 | 1/2003 | Degroot et al. | |
| 2003/0204210 | A1 | 10/2003 | Ousdigian et al. | |
| 2004/0106956 | A1* | 6/2004 | Sharma et al. ................. 607/9 |

* cited by examiner

*Primary Examiner*—Carl Layno
*Assistant Examiner*—Shevon E Johnson
(74) *Attorney, Agent, or Firm*—Michael C. Soldner

(57) ABSTRACT

A method and medical device for discriminating an arrhythmia that includes an input circuit sensing cardiac signals and a microprocessor identifying an event associated with the sensed cardiac signals as a first arrhythmia event. A first circuit delivers a first therapy, substantially simultaneous with coupling of a charging circuit and an energy storage device to generate stored energy on the energy storage device, in response to the first arrhythmia event, and a control circuit controls delivery of the first therapy by the first circuit. The microprocessor evaluates a physiologic response to the delivered first therapy and determines the event is other than the first arrhythmia event in response to the evaluated physiologic response.

9 Claims, 11 Drawing Sheets

DYNAMIC DISCRIMINATION UTILIZING ANTI-TACHY PACING THERAPY IN AN IMPLANTABLE MEDICAL DEVICE

FIELD OF THE INVENTION

The present invention relates generally to implantable medical devices, and, more particularly, to a method and apparatus for providing arrhythmia discrimination in an implantable medical device.

BACKGROUND OF THE INVENTION

Implantable cardioverter-defibrillator (ICD) art has long distinguished ventricular tachyarrhythmias by rate and type. Ventricular tachycardias (VTs), which are typically identified by their rate, can be further differentiated by their ECG configuration as either monomorphic or polymorphic. Arrhythmias with rates above an upper VT range, and up to a predetermined rate limit, are often termed flutter waves. Ventricular tachyarrhythmias at rates higher than the predetermined rate limit are classified as ventricular fibrillation (VF).

To treat each type of arrhythmia with an appropriate therapy, ICDs have been equipped with "tiered therapies". ICDs generally differentiate arrhythmias by rates, with programmable therapies to treat a respective type of detected arrhythmia(s). In such devices, arrhythmias such as VT are treated by delivering a series of low-power pacing pulses to the heart at a relatively high rate. This therapy is often referred to as anti-tachyarrhythmia pacing therapy (ATP). In contrast, arrhythmias such as VF, cannot be pace-terminated and are therefore treated using a more aggressive shock therapy. For example, many ICDs may be programmed to first treat a VT with low-power ATP and then, if the VT is not terminated by ATP or accelerates to ventricular flutter or fibrillation, deliver one or more high-power cardioversion or defibrillation shocks.

The rates of VT and VF overlap. Since VF poses the greater hazard to the patient, the rate used to discriminate VT and VF is selected to rarely classify VF as VT. For this reason, VTs having rates above a predetermined rate are often treated by high-energy shocks for VF when, in fact, they are monomorphic VTs that might be successfully terminated by low-energy ATP therapy. As a result, some patients must unnecessarily endure the pain of receiving a high-voltage shock delivery when painless ATP could have successfully terminated the rhythm.

What is needed therefore is a method and apparatus for discriminating arrhythmia events to reduce the utilization of high-voltage shocks.

BRIEF DESCRIPTION OF THE DRAWINGS

Aspects and features of the present invention will be readily appreciated as they become better understood by reference to the following detailed description when considered in connection with the accompanying drawings, wherein.

DETAILED DESCRIPTION OF THE DRAWINGS

Figure 1:
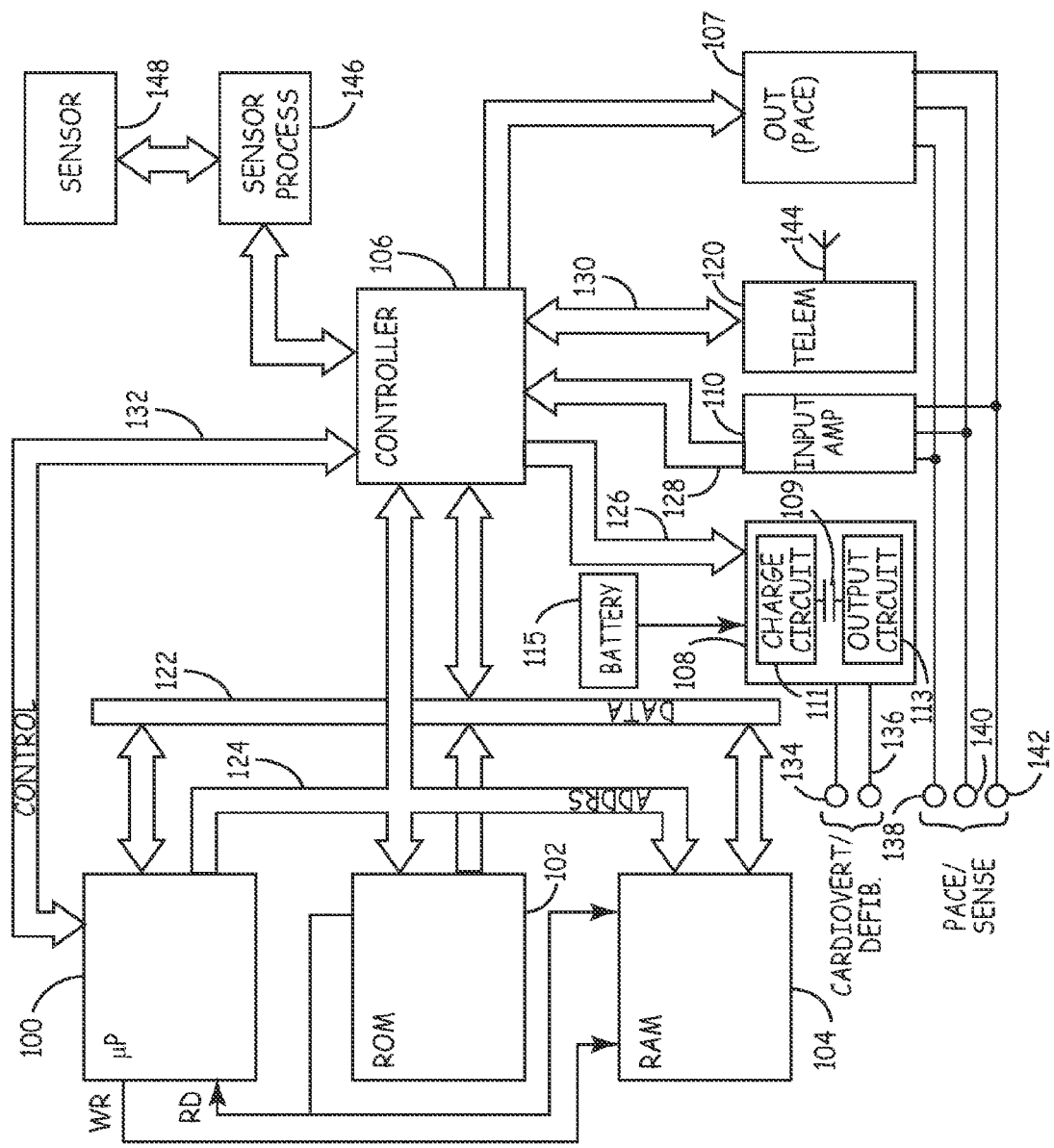
FIG. 1 is a block diagram of an illustrative embodiment of an implantable medical device in which the present invention may be employed.

FIG. 1 is a block diagram of an illustrative embodiment of an implantable medical device in which the present invention may be employed. As illustrated in FIG. 1, the device is embodied as a microprocessor based stimulator. However, other digital circuitry embodiments and analog circuitry embodiments are also believed to be within the scope of the invention. For example, devices having general structures as illustrated in U.S. Pat. No. 5,251,624 issued to Bocek et al., U.S. Pat. No. 5,209,229 issued to Gilli, U.S. Pat. No. 4,407,288, issued to Langer et al, U.S. Pat. No. 5,662,688, issued to Haefner et al., U.S. Pat. No. 5,855,593, issued to Olson et al., U.S. Pat. No. 4,821,723, issued to Baker et al. or U.S. Pat. No. 4,967,747, issued to Carroll et al., all incorporated herein by reference in their entireties, may also be usefully employed in conjunction with the present invention. Similarly, while the device of FIG. 1 takes the form of a ventricular pacemaker/cardioverter, the present invention may also be usefully employed in a device having atrial pacing and cardioversion capabilities. FIG. 1 should thus be considered illustrative, rather than limiting with regard to the scope of the invention.

The primary elements of the implantable medical device illustrated in FIG. 1 are a microprocessor 100, read-only memory (ROM) 102, random-access memory (RAM) 104, a digital controller 106, an input amplifier circuit 110, two output circuits 108 and 107, and a telemetry/programming unit 120. Read-only memory 102 stores the basic programming for the device, including the primary instruction set defining the computations performed to derive the various timing intervals employed by the cardioverter. RAM 104 generally serves to store variable control parameters, such as programmed pacing rate, programmed cardioversion intervals, pulse widths, pulse amplitudes, and so forth which are programmed into the device by the physician. Random-access memory 104 also stores derived values, such as the stored time intervals separating tachyarrhythmia pulses and the corresponding high-rate pacing interval.

Controller 106 performs all of the basic control and timing functions of the device. Controller 106 includes at least one programmable timing counter, which is initiated upon detection of a ventricular contraction, and which times intervals thereafter. This counter is used to generate the basic timing intervals used to deliver anti-tachy pacing (ATP)

pulses, and to measure other intervals used within the context of the current invention. On time-out of the pacing escape interval or in response to a determination that a cardioversion or defibrillation pulse is to be delivered, controller 106 triggers the appropriate output pulse from high-voltage output stage 108, as discussed below.

Following generation of stimulus pulses, controller 106 may be utilized to generate corresponding interrupts on control bus 132, waking microprocessor 100 from its "sleep" state, allowing microprocessor 100 to perform any required mathematical calculations, including all operations associated with evaluation of return cycle times and selection of anti-tachyarrhythmia therapies according to the present invention. The timing/counter circuit in controller 106 also controls timing intervals such as ventricular refractory periods, as is known in the art. The time intervals may be determined by programmable values stored in RAM 104, or values stored in ROM.

Controller 106 also generates interrupts for microprocessor 100 on the occurrence of sensed ventricular depolarizations or beats. On occurrence of a sensed ventricular depolarization, in addition to an interrupt indicating its occurrence placed on control bus 132, the then-current value of the timing/counter within controller 106 is placed onto data bus 122. This value may be used by microprocessor 100 in determining whether a tachyarrhythmia is present, and further, in determining the intervals separating individual tachyarrhythmia beats.

Output stage 108 contains a high-output pulse generator capable of generating shock therapy to be applied to the patient's heart via electrodes 134 and 136, which are typically large surface area electrodes mounted on or in the heart, or located subcutaneously. Other electrode configurations may also be used, including two or more electrodes arranged within and around the heart. Typically the high output pulse generator includes one or more high-voltage capacitors 109, a charging circuit 111 for transferring energy stored in a battery 115 to the high-voltage capacitors 109, an output circuit 113 and a set of switches (not shown) to allow delivery of monophasic or biphasic cardioversion or defibrillation pulses to the electrodes employed.

In addition to output circuit 108, output circuit 107 is provided to generate pacing pulses. This circuit contains a pacing pulse generator circuit that is coupled to electrodes 138, 140 and 142, and which are employed to accomplish cardiac pacing, including ATP pacing pulses, by delivery of a electrical stimulation between electrode 138 and one of electrodes 140 and 142. Electrode 138 is typically located on the distal end of an endocardial lead, and is typically placed in the apex of the right ventricle. Electrode 140 is typically an indifferent electrode mounted on, or adjacent to, the housing of the cardioverter defibrillator. Electrode 142 may be a ring or coil electrode located on an endocardial lead slightly proximal to the tip electrode 138, or it may be another electrode positioned inside or outside the heart. Although three electrodes 138-142 are shown in FIG. 1 for delivering pacing pulses, it is understood that the present invention may be practiced using any number of electrodes positioned in any pacing electrode configuration known in the art. Output circuit 108 may be controlled by control bus 126, which allows the controller 106 to determine the time, amplitude and pulse width of the pulse to be delivered. This circuit may also determine which electrode pair will be employed to deliver the pulse.

Sensing of ventricular depolarizations (beats) is accomplished by input amplifier 110, which is coupled to electrode 138 and one of electrodes 140 and 142. Signals indicating both the occurrence of natural ventricular beats and paced ventricular beats are provided to the controller 106 via bus 128. Controller 106 passes data indicative of the occurrence of such ventricular beats to microprocessor 100 via control bus 132 in the form of interrupts, which serve to wake up microprocessor 100. This allows the microprocessor to perform any necessary calculations or to update values stored in RAM 104.

Optionally included in the device is one or more physiologic sensors 148, which may be any of the various known sensors for use in conjunction with implantable stimulators. For example, sensor 148 may be a hemodynamic sensor such as an impedance sensor as disclosed in U.S. Pat. No. 4,865,036, issued to Chirife or a pressure sensor as disclosed in U.S. Pat. No. 5,330,505, issued to Cohen, both of which are incorporated herein by reference in their entireties. Alternatively, sensor 148 may be a demand sensor for measuring cardiac output parameters, such as an oxygen saturation sensor disclosed in U.S. Pat. No. 5,176,137, issued to Erickson et al. or a physical activity sensor as disclosed in U.S. Pat. No. 4,428,378, issued to Anderson et al., both of which are incorporated herein by reference in their entireties. Sensor processing circuitry 146 transforms the sensor output into digitized values for use in conjunction with detection and treatment of arrhythmias.

External control of the implanted cardioverter/defibrillator is accomplished via telemetry/control block 120 that controls communication between the implanted cardioverter/pacemaker and an external device, such as a communication network or an external programmer, for example. Any conventional programming/telemetry circuitry is believed workable in the context of the present invention. Information entering the cardioverter/pacemaker from the programmer is passed to controller 106 via bus 130. Similarly, information from the cardioverter/pacemaker is provided to the telemetry block 120 via bus 130.

Figure 2:
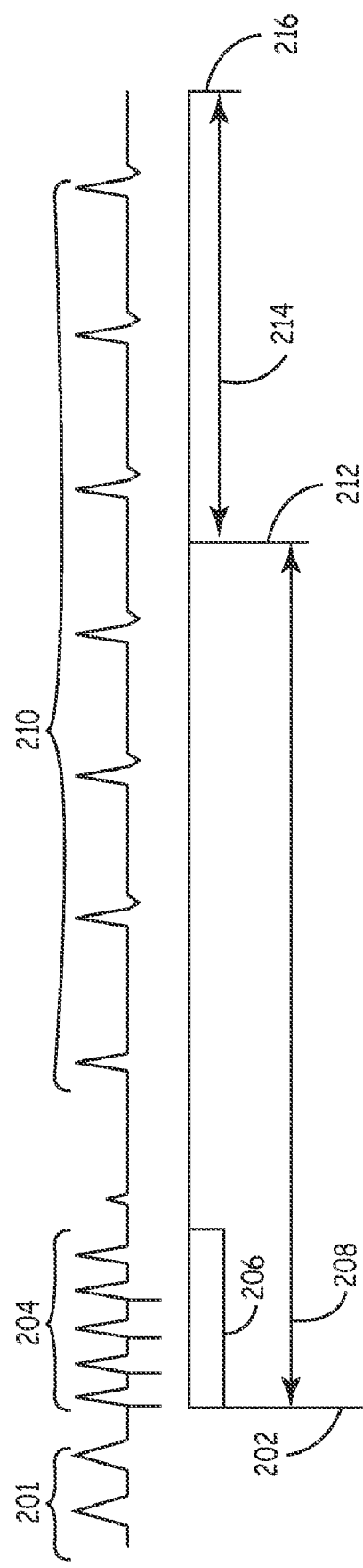
FIG. 2 is a timing diagram illustrating operation of the current inventive system in ATP During Capacitor Charging (ATP-DCC) mode.

FIG. 2 is a timing diagram illustrating operation of the current inventive system in ATP During Capacitor Charging (ATP-DCC) mode. After detection of a VT cardiac rhythm 201, capacitor charging 208 and ATP therapy delivery 204 may begin substantially simultaneously. High-rate VT 201, which in one embodiment is defined to include rhythms between 185 and 260 beats per minute (bpm), is treated by one sequence of Burst or Ramp or other type ATP-DCC therapy 204 that may extend for a predetermined period of time 206, or alternatively, for a predetermined number of pacing pulses. In FIG. 2, ATP-DCC therapy causes the VT rhythm to terminate, or "break", so that a normal sinus rhythm 210 is resumed.

When operation is occurring in ATP-DCC mode, all, or substantially all, of the ATP therapy is delivered while capacitor charging occurs. FIG. 2 shows charging 208 of high-voltage capacitors extending until charge time end 212 in preparation for delivery of a shock, if necessary. This shock may or may not be delivered at time 216, depending on whether normal sinus rhythm 210 has resumed. If it is determined that shock therapy is necessary, the shock will be delivered after synchronization with cardiac depolarizations has been completed during time 214, if possible. This synchronization attempts to deliver the shock at the appropriate time during the cardiac rhythm, such as coincident with the intrinsic R-wave.

As noted above, ATP-DCC therapy may cause the VT rhythm to terminate. This termination generally occurs in two ways. A "type 1" break occurs almost immediately after the last pacing pulse of an ATP therapy. In contrast, a "type 2" break involves several extra VT depolarizations following the last pacing pulse. In the case of a type 1 break, the detection of successful termination requires that the capacitors abort their charge. With a type 2 break, the ICD detection algorithm may not detect the return to normal sinus rhythm in time to prevent an unneeded shock delivery.

In the case of either type 1 or type 2 breaks discussed above, the device battery is drained of a certain percentage of its power even though ATP therapy is successful. In an ICD device capable of delivering between 100-150 full-energy shocks, a patient experiencing ten ATP-terminated episodes during any one follow-up period drains up to ten percent of the device battery power in a short amount of time if ATP-DCC is utilized. Moreover, this problem is not uncommon. Studies have shown that approximately fifteen percent of patients have more than ten episodes during a six-month period of time. Some patients have been known to exceed this number, potentially expending the battery supply during the first six months of implant.

Figure 3:
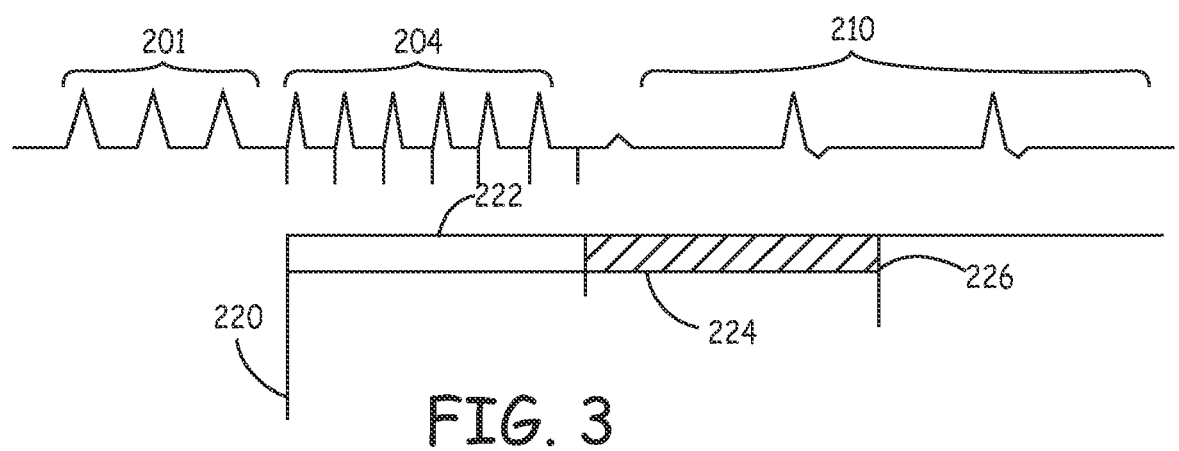
FIG. 3 is an exemplary timing diagram illustrating operation of the current inventive system in ATP Before Capacitor Charging (ATP-BCC) mode.

FIG. 3 is an exemplary timing diagram illustrating operation of the current inventive system in ATP Before Capacitor Charging (ATP-BCC) mode. When operating in ATP-BCC mode, all, or substantially all, of the ATP therapy delivery occurs prior to capacitor charging. FIG. 3 illustrates delivery of ATP therapy 204 initiated at time 220 following detection of a VT episode 201. Therapy continues during time 222. In this case, ATP therapy returns the patient to normal sinus rhythm 210. The ICD device detects the break in VT by the change in cardiac rate as well as the return to normal sinus rhythm 210 during verification period 224. As a result, no charging of the high-voltage capacitors is initiated at time 226.

According to the current invention, operation of the ICD may transition from ATP-DCC mode shown in FIG. 2 to execution in ATP-BCC mode shown in FIG. 3 based on programmable criteria. In one embodiment, this "Charge Saver" function switches the ICD device operation from ATP-DCC to ATP-BCC mode after attaining a user-programmed consecutive number of ATP successes since the previous follow-up session. ATP therapy is generally considered successful when the VT breaks/aborts prior to shock delivery, although other criteria may be defined for determining the success of the ATP therapy. The device will revert back to ATP-DCC mode following a predetermined criteria, which may include a predetermined number of failures to break a VT in the ATP-BCC operational mode, as will be describe in more detail in reference to FIG. 4.

Figure 4:
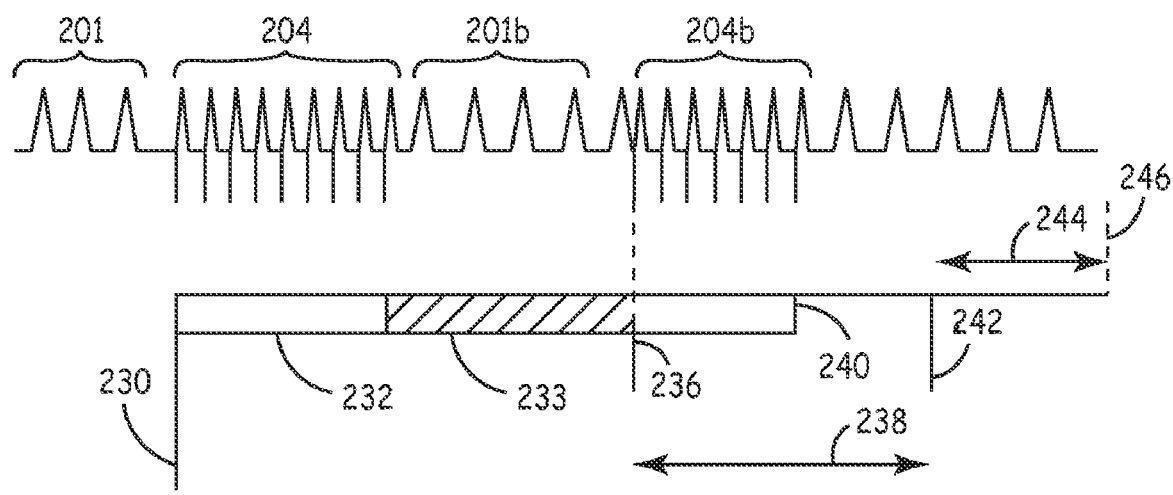
FIG. 4 is an exemplary timing diagram illustrating an ongoing VT episode that fails to break following ATP-BCC therapy.

FIG. 4 is an exemplary timing diagram illustrating an ongoing VT episode that fails to break following ATP-BCC therapy. ATP-BCC therapy 204 is delivered during time 232 following VT detection 201. Thereafter, verification period 233 confirms the ongoing VT episode 201b. Charging of high-voltage capacitors 238 begins substantially at time 236. According to one embodiment of the invention, a second sequence of ATP therapy 204b may be delivered during capacitor charging. Studies such as the Medtronic PainFREE $R_x$ study have shown that this additional ATP sequence has a low likelihood of accelerating the ventricular rate, and in fact, has the potential for terminating a VT episode.

Capacitor charging during time 238 has a variable duration, depending on the programmed energy value. At charge end time 242, a non-committed synchronization period 244 begins. During this synchronization period 244, the patient's cardiac rhythm is evaluated to locate an appropriate time to deliver a shock. The shock will be delivered at the end of the synchronization period unless it is determined that the VT episode has terminated. If the episode has terminated, the charge on the capacitors would be dumped or drained at the end of the capacitor charge time 238 or sometime thereafter.

According to another aspect of the current invention, if a predetermined number of episodes of VT are not terminated by ATP-BCC therapy such that shock delivery occurs as shown in FIG. 4, the system reverts from ATP-BCC mode to the ATP-DCC mode. This allows shock delivery to occur without delay following the unsuccessful delivery of ATP.

Figure 5:
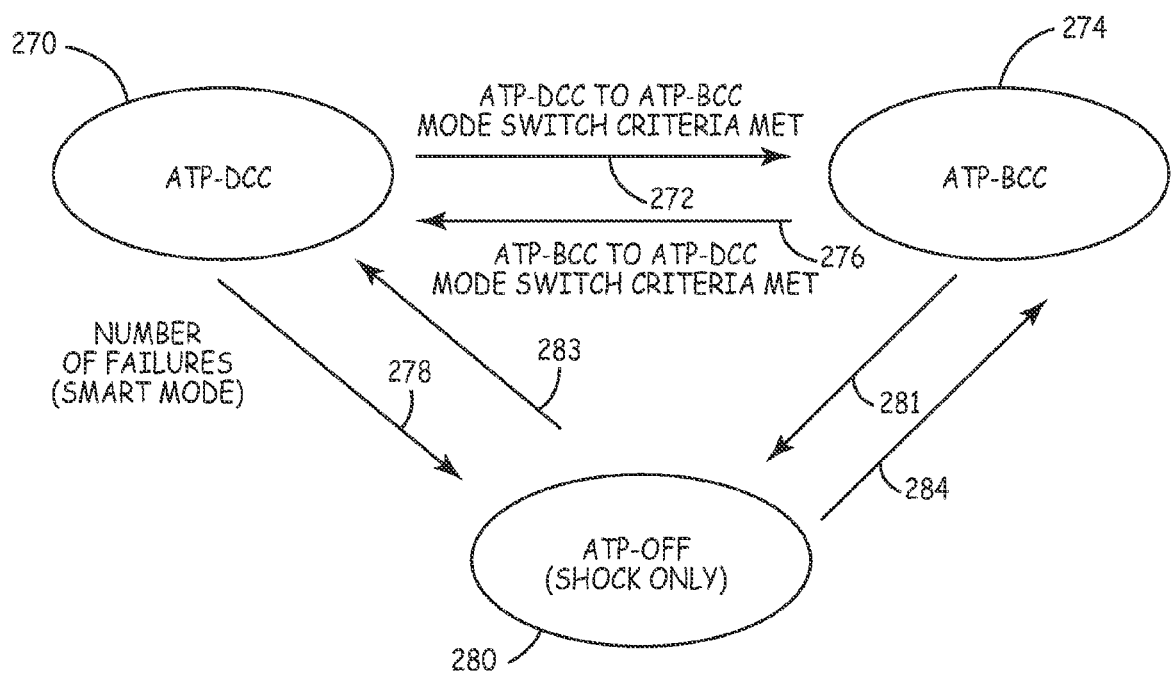
FIG. 5 is a state diagram illustrating transitions between therapy modes, according to the present invention.

FIG. 5 is a state diagram illustrating the manner in which the system transitions between ATP therapy modes. ICD can be programmed with ATP-DCC mode and the Charge Saver feature enabled, for example, as illustrated by state 270, as well as the Charge Saver feature. At the time of implant, the physician may choose whether to disable the Charge Saver feature. In one embodiment of the invention, other programmable parameters may be selected by the physician if the Charge Saver feature is enabled. These parameters may include the number of successful ATP-DCC therapy sessions that must be delivered prior to the automated activation of ATP-BCC mode, as will be discussed further below.

During operation with Charge Saver enabled and the system operating in ATP-DCC, a transition to ATP-BCC mode shown as state 274 may be triggered by the delivery of a predetermined number X ATP-DCC therapy sessions that succeed in breaking the VT rhythm. This transition is depicted by arrow 272. Conversely, when operating in ATP-BCC mode and after a predetermined number Y failed ATP-BCC therapy attempts, the system transitions to ATP-DCC mode as shown by arrow 276. As discussed above, in one embodiment of the invention, X and Y are programmable. Alternatively, these numbers may be predetermined, non-programmable values. Finally, these numbers may represent consecutive ATP therapy sessions, or may involve a set of "S of T" therapy sessions. For example, a transition from ATP-DCC to ATP-BCC may be selected to occur if 4 of 5 ATP-DCC therapy sessions are determined to be successful.

Other trigger criteria may be used instead of, or in addition to, the above criteria to initiate a switch between ATP-DCC and ATP-BCC modes. In one embodiment, the system stores both cycle length (CL) and/or R-wave morphology of a VT rhythm to determine whether the type of VT currently being experienced is the same type of VT that occurred during a recently-detected episode or episodes. This is important since patients can exhibit different types of VT, each of which may respond differently to ATP therapy. If the characteristics of the current episode are the same as the previous episode, and the previous episode responded favorably to ATP-BCC therapy, the device remains in the ATP-BCC mode of operation upon detection of a break in rate. On the other hand, if the CL and/or R-wave morphology has changed, the system may be programmed to revert back to the ATP-DCC mode of operation.

According to the foregoing embodiment, different mode transition criteria may be specified for each type of VT rhythm. For example, a transition from ATP-DCC to ATP-BCC therapy may be triggered by M consecutive successful therapy sessions for a first type of VT. This same mode transition may be triggered by M' of N successful therapy sessions for a second type of VT. This allows therapies to be individually selected for different types of VT rhythms.

In yet another embodiment, the system mode-switching criteria takes into account VT frequency. As discussed above, some patients experience "VT storms" involving the occurrence of a large number of episodes within a short period of time, such as hours or even minutes. Such episodes, which usually involve VT rhythms having similar cycle lengths and morphologies, may significantly impact battery resources. In this embodiment, the occurrence of a predetermined number of VT episodes in a predetermined time period may trigger a switch from ATP-DCC to ATP-BCC mode to save battery resources.

According to an alternative embodiment of the invention, a programmable threshold duration is used to detect VT storms. If two consecutive VT episodes occur within this predefined threshold duration, a count is incremented. If the count reaches a predetermined value within some larger programmable time period, a mode switch may be triggered. Once a mode switch to ATP-BCC mode occurs, continued operation in ATP-BCC mode may be predicated on obtaining a predetermined success rate using any of the mechanisms discussed above. Alternatively, another threshold time can be defined to track episode frequency in the ATP-BCC mode such that if the inter-episode duration exceeds this value, a transition back to ATP-DCC mode occurs.

If desired, waveform morphology criteria may be applied to VT storm detection. For example, VT episodes that are separated by longer periods of time such as weeks or months may involve different types of VT rhythms. Therefore, for all VT episodes, or just the VT episodes separated by a predetermined time period, mode-switch criteria may be individually specified for respective types of VT rhythms as discussed above.

Transition from ATP-DCC to ATP-BCC mode or vice versa could also be predicated on the length of an episode. For example, the episode length measured from first detection to the termination of a rhythm could be used as the mode-switching criteria. In one embodiment, longer episodes could trigger a transition to ATP-DCC mode.

According to yet another aspect of the invention, the detection of VT storms may trigger a patient alert (audible, vibratory or other). For example, the patient may be notified to contact a physician so that operating parameters of the system may be re-evaluated, and mode-switching conditions may be re-programmed, if necessary.

Another aspect of the invention relates to an optional programmable feature for disabling all modes of ATP. If this "Smart Mode" feature is enabled and a predetermined criteria is met, all ATP therapy is disabled. In one embodiment, this Smart Mode feature operates when execution is occurring in ATP-DCC mode and a predetermined number of failed therapy attempts is detected. This transition is shown by arrow 278 and state 280. The number of failed therapy attempts needed to trigger this transition may be programmable, or may be a predetermined number, which is preferably "four". Thereafter, the ICD device will only deliver the programmed shock therapy. In another embodiment, this feature could also be provided when execution is occurring in ATP-BCC mode, as shown by arrow 281. In yet another embodiment, the switch from either ATP-BCC or ATP-DCC mode could be triggered by a VT rhythm or waveform morphology that meets a predetermined criteria. For instance, the transition to a mode wherein ATP is disabled may be triggered by detection of a fast VT rhythm that exceeds 250 bpm.

In one embodiment, after a transition occurs to a mode wherein ATP is disabled, shock therapy will continue until intervention is provided to re-activate the ATP-DCC mode. Such intervention may be provided, for example, during a subsequent follow-up session. In another embodiment, the system will continue operation in this mode until a defined criteria is met. For example, if the transition to the ATP-disabled mode occurs because of a fast VT rhythm, the system will revert back to the previous mode of operation after the fast VT episode has been terminated by the shock delivery, as shown by arrows 283 and 284.

Figure 6A:
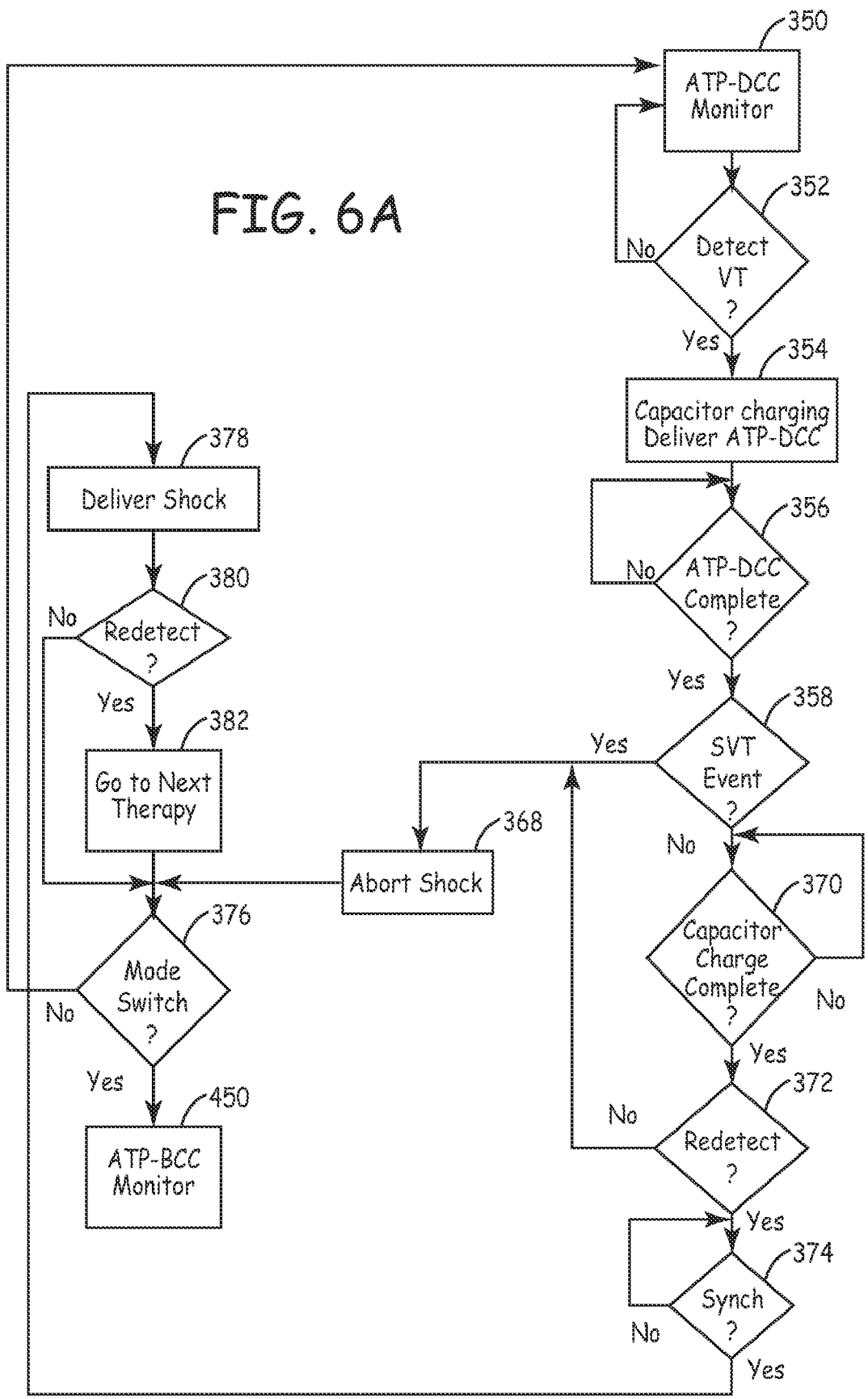
FIG. 6A is an exemplary flowchart of a method of discriminating a tachyarrhythmia event according to an embodiment of the present invention.

FIG. 6A is a flowchart of a method of discriminating a tachyarrhythmia event according to an embodiment of the present invention. As illustrated FIG. 6A, a device such as the one shown in FIG. 1 is generally implanted with ATP-DCC mode enabled, although it maybe implanted with ATP-BCC mode enabled, if desired. While the device is in the nominal ATP-DCC mode, block 350, the device continuously monitors for the presence of tachyarrhythmias, using known detection methods, such as those described above. Once a VT rhythm is detected, YES in block 352, for example, delivery of an ATP-DCC therapy sequence and charging of the high-voltage capacitors are initiated substantially simultaneously, block 354.

Once delivery of the ATP-DCC therapy is completed, YES in block 356, the VT rhythm is monitored to evaluate the physiologic response to the delivered ATP sequence, described in detail below in reference to FIG. 7, and a determination is made, based on the monitored physiologic response, as to whether the detected event is an SVT event, block 358, rather than a VT event as was originally determined during the detection in block 352.

Figure 7A:
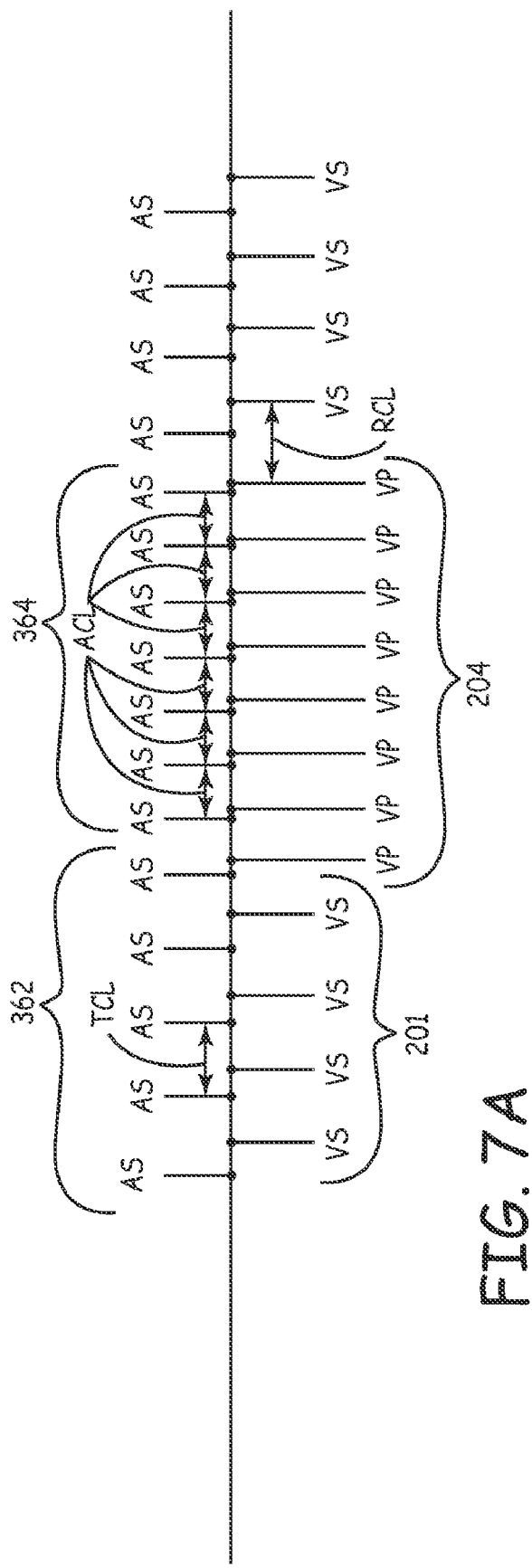
FIG. 7A is an exemplary timing diagram illustrating a method of discriminating a tachyarrhythmia event according to an embodiment of the present invention.
Figure 7B:
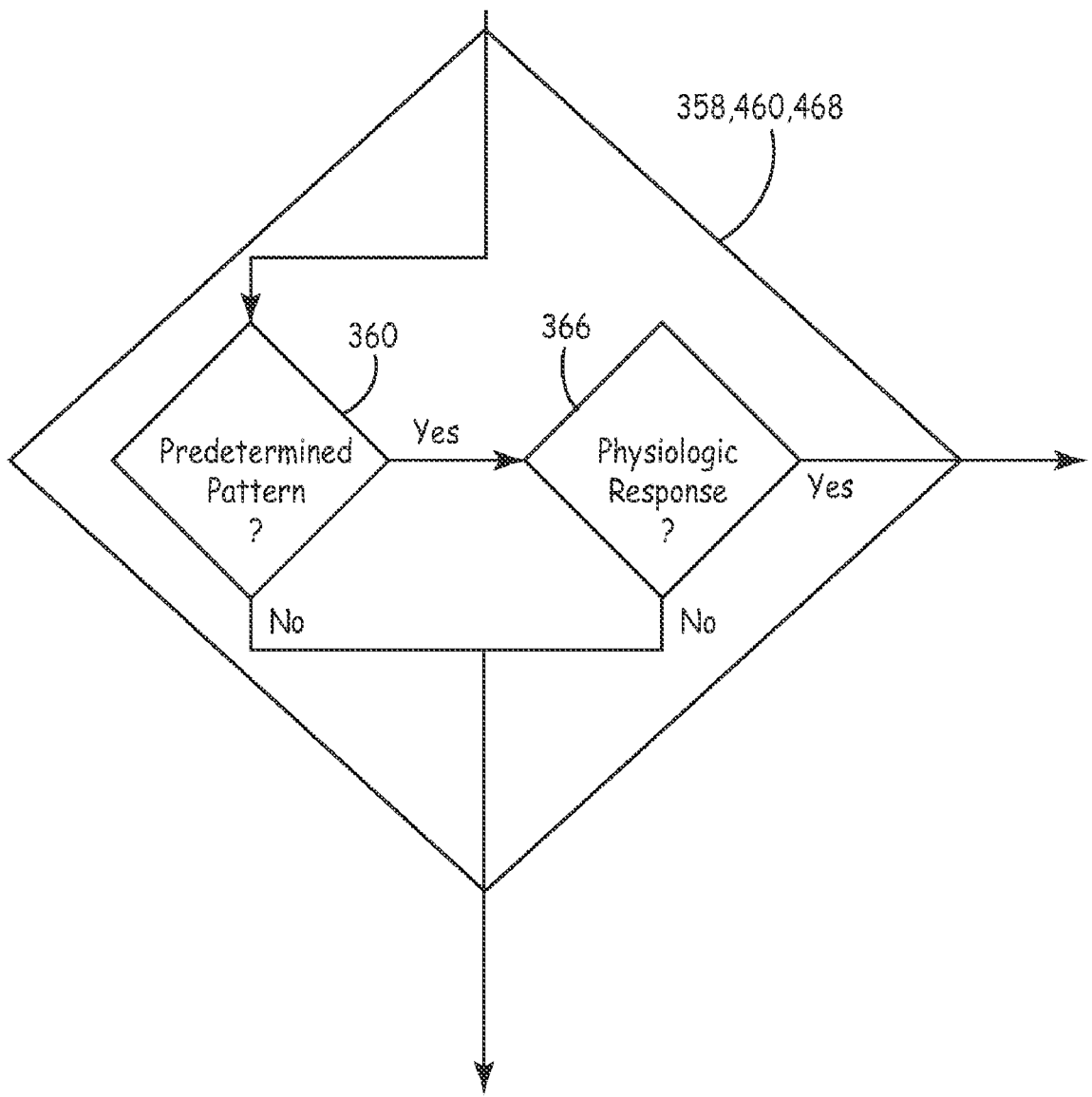
FIG. 7B is a flowchart of a method for discriminating a tachyarrhythmia event according to an embodiment of the present invention.

FIG. 7A is an exemplary timing diagram illustrating a method of discriminating a tachyarrhythmia event according to the present invention. FIG. 7B is a flowchart of a method for discriminating a tachyarrhythmia event according to the present invention. As illustrated in FIGS. 7A and 7B, according to an embodiment of the present invention, the determination in block 358 as to whether, based on the monitored physiologic response, the detected event is an SVT event is made by determining whether the PR interval pattern detected during the sensed event is consistent with an SVT needing additional discrimination, such as a 1:1 A:V pattern that could be either supraventricular or ventricular in origin, or a greater than 1:1 A:V pattern that could be either supraventricular or simultaneous supraventricular and ventricular tachycardia in origin, block 360. In one embodiment, if the predetermined PR pattern is detected, YES in block 360, a determination is made as to whether the absolute difference between a cycle length TCL associated with the atrial sensed events 362 sensed during the tachycardia rhythm detected (block 352) prior to delivery of the ATP-DCC sequence 204, and a cycle length ACL associated with each of the atrial sensed events 364 occurring during delivery of the ATP-DCC sequence 204 is less than or equal to a predetermined threshold, block 366. According to an embodiment of the present invention, the predetermined threshold in block 366 is set as 30 ms, although it is understood that the threshold is programmable and could be assigned any desired value.

According to an embodiment of the present invention, other factors in addition to pre-ATP therapy atrial cycle length TCL and atrial cycle length ACL associated with delivery of the ATP therapy may be included as physiological responses to be monitored to further discriminate the tachyarrhythmias event. For example, the determination as to whether the detected VT rhythm is actually an SVT event, block 358, could also include determining whether a return cycle length RCL corresponding to an initial ventricular sense event that occurs subsequent to the delivery of the ATP therapy 204 is greater than or equal to a predetermined percentage of the pre-ATP therapy atrial cycle length TCL. For example, according to an embodiment of the present invention, a determination is made as to whether the return cycle length RCL is greater than or equal to a percentage of the value of the pre-ATP therapy atrial cycle length TCL, such as 150% for example. According to another embodiment of the present invention, the determination could include determining whether the return cycle length RCL is greater than or equal to a fixed duration greater than the atrial cycle length TCL, or whether the return cycle length RCL is greater than or equal to an absolute fixed cycle length. In addition, the determination as to whether the detected VT rhythm is actually an SVT event could also include determining whether there is a post-paced rhythm pattern consistent with an VAAV (two atrial events occur within return cycle length RCL), VAV or VV response detected subsequent to delivery of the ATP therapy 204.

If the required physiological factors are satisfied in block 366, i.e., one or any combination of the absolute difference between cycle length TCL and cycle length ACL is less than or equal to the predetermined threshold, return cycle length RCL is greater than or equal to a threshold that is dependent upon pre-ATP therapy atrial cycle length TCL, return cycle length RCL is greater than or equal to an absolute fixed cycle length, and the post-pace rhythm pattern is consistent with SVT (e.g. VAAV, VAV or VV), then the VT event is determined to be an SVT event, YES in block 358, and delivery of the shock is aborted, block 368.

Returning to FIG. 6A, if the rhythm is not determined to be an SVT event, NO in block 358, and therefore continues to be classified as a VT event, a determination is made as to whether the capacitors have been charged to a predetermined level, block 370. Once the capacitors are charged to the predetermined level, a non-committed synchronization period begins during which the patient's cardiac rhythm is evaluated to determine an appropriate time within the occurring VT rhythm to deliver the shock, block 374, and to determine if the VT rhythm is redetected, block 372. When the system is synchronized, shock delivery will occur unless the system has first determined that the VT rhythm has been terminated, i.e., is no longer detected, NO in block 372.

If the episode is no longer detected, NO in block 372, or if the event is not determined to be an SVT event in block 358, delivery of the shock is aborted, block 368 and a determination is made as to whether the device should transition from the ATP-DCC mode to the ATP-BCC mode, block 376, based on the factors described above in reference to FIG. 5. If it is determined that the device should not transition from the ATP-DCC mode to the ATP-BCC mode, NO in block 376, the process returns to block 350 to monitor for subsequent detected VT rhythms, at which point the process is repeated. If a mode switch is indicated, YES in block 376, the device transitions to the ATP-BCC mode, block 450, which is described below in reference to FIG. 6B.

Once the synchronization period is completed, YES in block 374, the shock is delivered, block 378. Upon completion of delivery of the shock therapy, a determination is made as to whether the VT rhythm was terminated by the delivered shock, block 380. Several criteria may be used to make this determination, including cardiac rate, cycle length, R-wave morphology, and/or any other criteria known in the art for this purpose. If the VT has not terminated, the device begins the process of delivering a next programmed therapy in a tiered therapy approach, assuming a tiered therapy approach is utilized, block 382. Once all of the programmed therapies have been exhausted in block 382, or in the case where a tiered approach is not utilized, and the shock was delivered in block 378, the determination is made as to whether the device should transition from the ATP-DCC mode to the ATP-BCC mode, block 376, based on the factors described above in reference to FIG. 5. If it is determined that the device should not transition from the ATP-DCC mode to the ATP-BCC mode, NO in block 376, the process returns to block 352 to monitor for subsequent detected VT rhythms, at which point the process is repeated. If a mode switch is indicated, YES in block 376, the device transitions to the ATP-BCC mode, block 450, which is described below in reference to FIG. 6B.

Figure 6B:
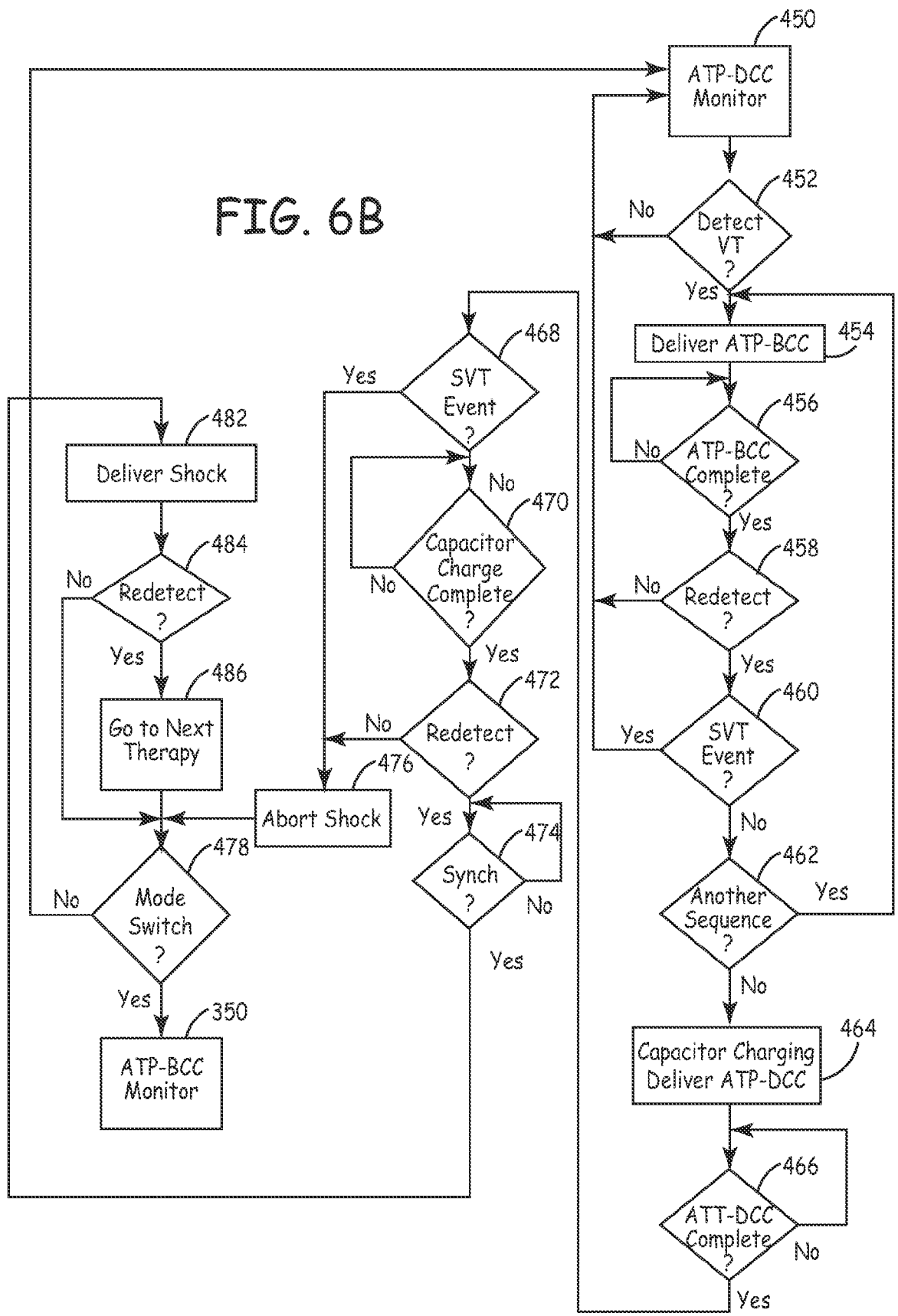
FIG. 6B is an exemplary flowchart of a method of discriminating a tachyarrhythmia event according to an embodiment of the present invention.

FIG. 6B is an exemplary flowchart of a method of discriminating a tachyarrhythmia event according to an embodiment of the present invention. As illustrated in FIG. 6B, when in the ATP-BCC mode state of operation, block 450, the device monitors for the presence of tachyarrhythmias, block 452. When a tachyarrhythmia meets VT criteria, for example, YES in block 452, an ATP-BCC therapy sequence is initiated without initiating charging of the capacitors 109, block 454. Once delivery of the initial ATP-BCC therapy sequence has completed, YES in block 456, a determination is made to whether the VT event is redetected, block 458, in order to determine whether the initial ATP-BCC therapy session was successful at terminating the VT event. If the initial ATP-BCC sequence was successful and therefore the VT event is not redetected, NO in block 458, the process returns to block 450 to monitor for subsequent VT rhythms, at which point the process is repeated.

If the initial ATP-BCC sequence was not successful, YES in block 458, the VT rhythm is monitored to evaluate the physiologic response to the delivered ATP sequence, as described above, and a determination is made, based on the monitored physiologic response, as to whether the detected event is an SVT event, block 460, rather than a VT event as was originally determined during the detection in block 450-452, as described above. If, in response to the physiologic response to the delivered ATP-BCC sequence, the rhythm is determined to be an SVT, YES in block 460, the process returns to block 450 to monitor for subsequent VT rhythms, at which point the process is repeated. If the rhythm is not determined to be an SVT, NO in block 460, a determination is made as to whether another sequence of the ATP-BCC therapy should be delivered, block 462. According to the present invention, the number of ATP sequences that may be delivered prior to initiating the charging of high voltage capacitors and delivery of the ATP-DCC therapy of block 462 is programmable, and can include only a single sequence, or a multiple number of sequences, such as three for example. The number chosen may be dependent upon many factors or combination of factors, such as the rate of the detected rhythm, whether the detected rhythm is a stable rhythm, or whether the detected rhythm is part of a cluster of detected rhythms that occur in a specified period of time.

Once the programmed number of ATP-BCC sequences have been delivered, NO in block 462, delivery of an ATP-DCC therapy sequence and charging of the high-voltage capacitors are initiated substantially simultaneously, block 464. After delivery of the ATP-DCC therapy sequence has completed, YES in block 466, the VT rhythm is monitored to evaluate the physiologic response to the delivered ATP sequence, as described above, and a determination is made, based on the monitored physiologic response, as to whether the detected event is an SVT event, block 468, rather than a VT event as was originally determined during the detection in block 450-452, as described above. If, in response to the physiologic response to the delivered ATP-BCC sequence, the rhythm is determined to be an SVT, YES in block 468, the process returns to block 450 to monitor for subsequent VT rhythms, at which point the process is repeated.

If the rhythm is not determined to be an SVT, NO in block 468, a determination is made as to whether the capacitors have been charged to a predetermined level, block 470. Once the capacitors are charged to the predetermined level, a non-committed synchronization period begins during which the patient's cardiac rhythm is evaluated to determine an appropriate time within the occurring VT rhythm to deliver the shock, block 474, and to determine if the VT rhythm is redetected, block 472. When the system is synchronized, shock delivery will occur unless the system has first determined that the VT rhythm has been terminated, i.e., is no longer detected, NO in block 472.

If the episode is no longer detected, NO in block 472, delivery of the shock is aborted, block 476 and a determination is made as to whether the device should transition from the ATP-DCC mode to the ATP-BCC mode, block 478, based on the factors described above in reference to FIG. 5. If it is determined that the device should not transition from the ATP-DCC mode to the ATP-BCC mode, NO in block 478, the process returns to block 450 to monitor for subsequent detected VT rhythms, at which point the process is repeated. If a mode switch is indicated, YES in block 478, the device transitions to the ATP-DCC mode, block 350, which is described above in reference to FIG. 6A.

Once the synchronization period is completed, YES in block 474, the shock is delivered, block 482. Upon completion of delivery of the shock therapy, a determination is made as to whether the VT rhythm was terminated by the delivered shock, block 484. Several criteria may be used to make this determination, including cardiac rate, cycle length, R-wave morphology, and/or any other criteria known in the art for this purpose. If the VT has not terminated, the device begins the process of delivering a next programmed therapy in a tiered therapy approach, assuming a tiered therapy approach is utilized, block 486. Once all of the programmed therapies have been exhausted in block 486, or in the case where a tiered approach is not utilized, and the shock was delivered in block 482, or if the VT rhythm is no longer detected after the shock is delivered, NO in block 484, the determination is made as to whether the device should transition from the ATP-BCC mode to the ATP-DCC mode, block 478, based on the factors described above in reference to FIG. 5. If it is determined that the device should not transition from the ATP-BCC mode to the ATP-DCC mode, NO in block 478, the process returns to block 450 to monitor for subsequent detected VT rhythms, at which point the process is repeated. If a mode switch is indicated, YES in block 478, the device transitions to the ATP-DCC mode, block 350, which is described above in reference to FIG. 6A.

Figure 8:
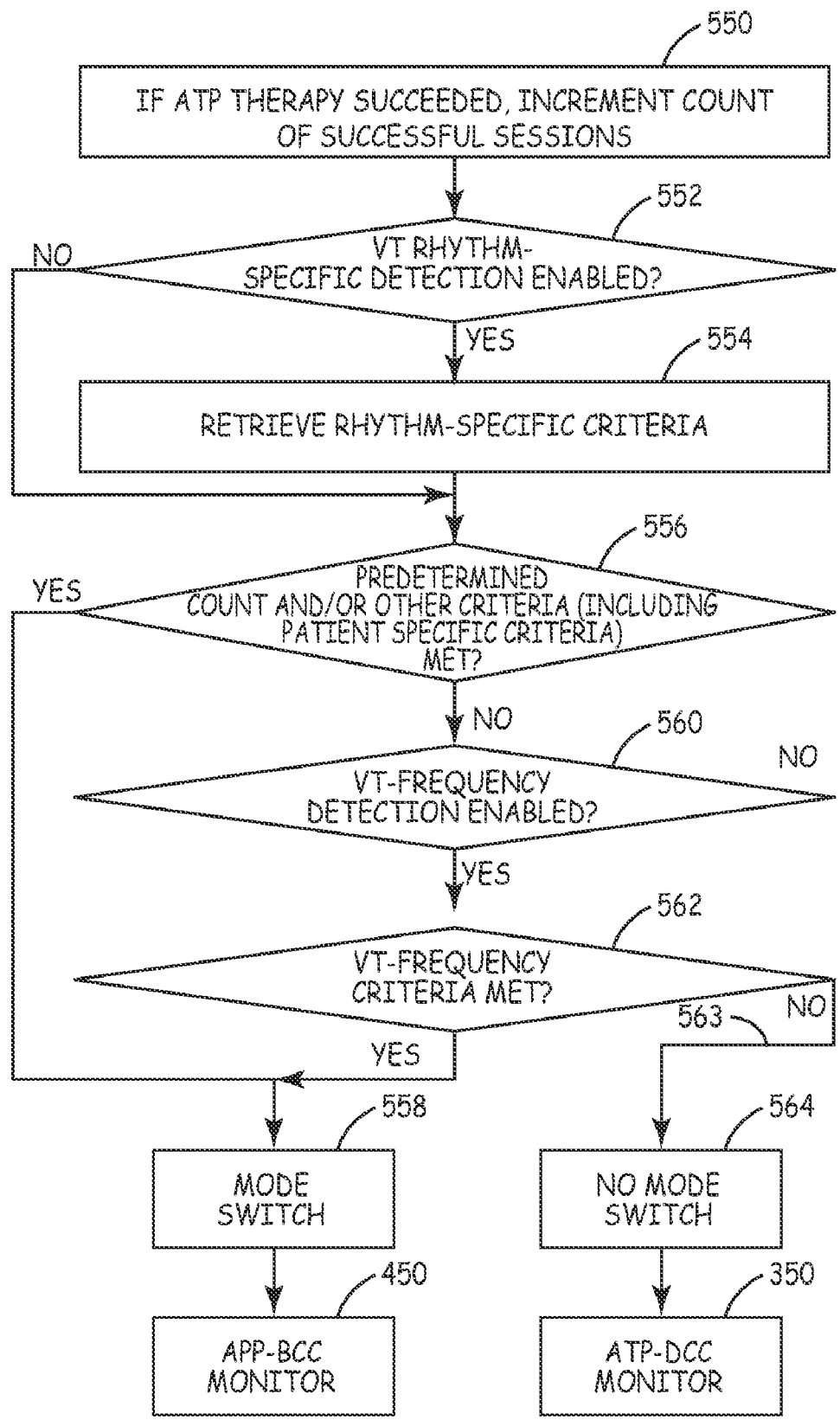
FIG. 8 is a flowchart illustrating a mode switch according to an embodiment of the present invention.

FIG. 8 is a flowchart illustrating a mode switch according to an embodiment of the present invention. As illustrated in FIG. 8, in order to determine whether to transition from the ATP-DCC mode to the ATP-BCC mode in block 372 of FIG. 6A, a count of successful ATP therapy sessions is incremented each time the most-recently provided ATP therapy terminates the VT rhythm, block 550. A determination is then made as to whether rhythm-specific criteria will be used to make the mode-switch determination, block 552. As described above, it may be desirable to define specific criteria for the various types of VT rhythms, as may be identified by cycle length, and waveform morphology.

If rhythm-specific criteria will be utilized, the VT rhythm associated with the most recent VT episode is analyzed, and the corresponding criteria retrieved, as shown in block 554. Otherwise, the standard criterion is utilized. This criterion may be programmable, or a pre-set value.

After the criterion is selected, if necessary, the count of successful ATP therapy sessions is compared against the appropriate criteria in block 556 to determine whether a mode switch should be performed. It may be noted that this criteria may involve a consecutive number of successes, a predetermined number of successes in a predetermined period of time, or may instead require X of Y successes, as discussed above. Other criteria that do, or do not, involve a count of successful therapy-delivery sessions may be used instead of, or in addition to, the predetermined count criteria. For example, the duration of a VT episode may be utilized to trigger a mode switch to ATP-BCC mode, if desired. As will be discussed further below, this criteria may include patient-specific criteria. If the pre-defined criteria are met, the mode switch from the ATP-DCC mode, block 350, to the ATP-BCC mode, block 450, is performed, block 558.

If the predetermined criteria are not met in decision block 556, a determination is made as to whether VT-frequency monitoring is enabled, block 560 so that VT storms may be detected. If VT-frequency monitoring is enabled, a determination is made as to whether the VT-frequency criteria are met, block 562. This involves making a determination as to whether a predetermined number of VT episodes are detected in a specific period of time. Alternatively, an inter-episode threshold duration may be defined to detect VT storms in the manner discussed above. The detection may also take into consideration types of VT episodes, if desired. For example, separate running counts may be maintained for various types of VT episodes, with the types being determined by CL and waveform morphology. Each type of episode may also be associated with different criteria in a manner similar to that discussed. For example, a VT storm indication may be met if a first type of VT episode occurs X times in Y minutes, whereas a VT storm indication is met for a second type of VT episode occurring X' times in Y' minutes, and so on.

If any of the one or more VT-frequency criteria is met, a mode switch from ATP-DCC therapy mode to ATP-BCC therapy mode occurs, block 558, and processing continues in ATP-BCC mode, block 450 of FIG. 6B. Otherwise, if VT-frequency detection is not enabled, or the VT-frequency criteria are not met, no mode switch occurs, block 564, and processing continues in ATP-DCC mode, block 350 of FIG. 6A.

Figure 9:
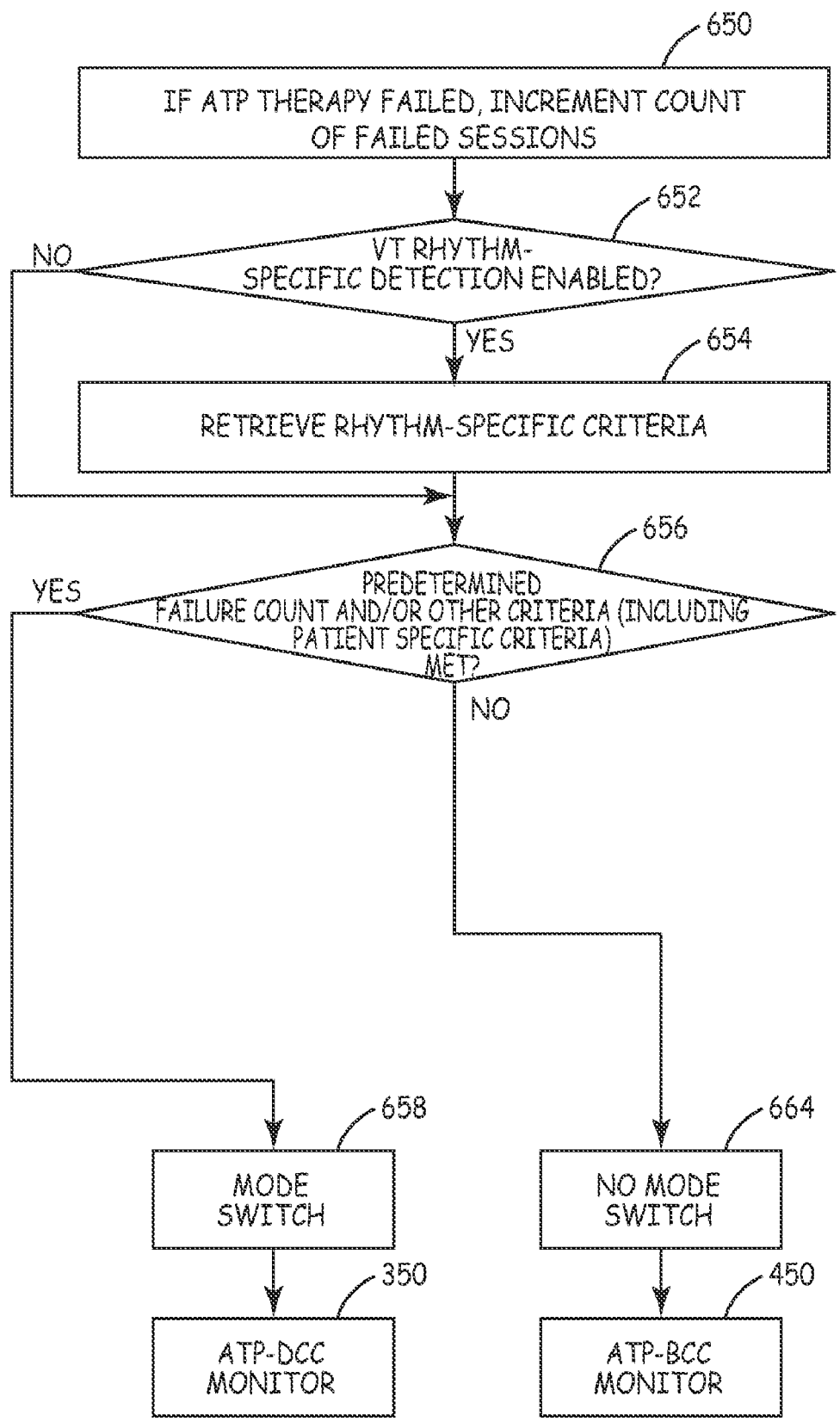
FIG. 9 is a flowchart illustrating a mode switch according to an embodiment of the present invention.

FIG. 9 is a flowchart illustrating a mode switch according to an embodiment of the present invention. As illustrated in FIG. 9, in order to determine whether to transition from the ATP-BCC mode to the ATP-DCC mode in block 478 of FIG. 6B, a count of unsuccessful ATP therapy sessions is incremented each time that the most-recently provided ATP therapy fails to terminate the VT rhythm, block 650. A determination is then made as to whether rhythm-specific criteria will be used to make the mode-switch determination, block 652. As described above, different criteria may be defined for different VT rhythms.

If rhythm-specific criteria will be utilized, the VT rhythm associated with the most recent VT episode is analyzed, and the corresponding criteria retrieved, as shown in block 654. Such rhythm-specific criteria may involve a mode switch from ATP-BCC to ATP-DCC mode based on the detection of a particular type of VT episode, for instance. In another instance, the rhythm-specific criteria may involve a count of a number of failed therapy attempts, for example.

If rhythm-specific criteria are not to be utilized as determined in block 652, a standard criterion may be utilized. In either case, the appropriate criteria are used in block 656 to determine whether a mode switch from the ATP-BCC therapy mode to the ATP-DCC therapy mode should be performed. It may be noted that this criteria may involve a consecutive number of failed therapy attempts, may instead require X of Y failed therapy attempts, or may require a predetermined number of failures in a predetermined amount of time as discussed above. In one embodiment, a predetermined number of failed therapy attempts from the last patient medical check-up may be utilized as the trigger criteria. In another embodiment, the criteria may alternatively or additionally include conditions unrelated to failed therapy attempts, such as the occurrence of a particular type of rhythm, or a specific change in a type of rhythm, as noted above. This criteria may also include patient-specific conditions related to patient medical history. If this criteria is met, YES in block 656, the mode switch is performed, block 658, and processing continues in ATP-DCC therapy mode, block 350 of FIG. 6A. If the criteria are not met, no mode switch is performed, block 564, and processing continues in the ATP-BCC therapy mode, block 450 of FIG. 6B.

As discussed above, many different types of criteria may be used to trigger a mode switch. In one embodiment, this criteria is programmable, and may be initially programmed and/or thereafter altered based on patient history. This allows system operation to be tailored for each patient. This could take into account, for example, a patient's individual response to ATP therapies. Programming can be accomplished, for example, using telemetry systems known in the art.

Some of the techniques described above may be embodied as a computer-readable medium comprising instructions for a programmable processor such as microprocessor 100 or control circuitry 106 shown in FIG. 1. The programmable processor may include one or more individual processors, which may act independently or in concert. A "computer-readable medium" includes but is not limited to any type of computer memory such as floppy disks, conventional hard disks, CD-ROMS, Flash ROMS, nonvolatile ROMS, RAM and a magnetic or optical storage medium. The medium may include instructions for causing a processor to perform any of the features described above for initiating a session of the escape rate variation according to the present invention.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than as specifically described, without departing from the scope of the present invention. As to every element, it may be replaced by any one of infinite equivalent alternatives, only some of which are disclosed in the specification.

The invention claimed is:

1. A medical device for discriminating arrhythmia events, comprising:
   an input circuit sensing cardiac signals;
   a microprocessor identifying an event associated with the sensed cardiac signals as a first arrhythmia event;
   a first circuit delivering a first therapy, substantially simultaneous with coupling of a charging circuit and an energy storage device to generate stored energy on the energy storage device, in response to the first arrhythmia event; and
   a control circuit controlling delivery of the first therapy by the first circuit, wherein the microprocessor evaluates a physiologic response to the delivered first therapy and determines the event is other than the first arrhythmia event in response to the evaluated physiologic response, wherein the microprocessor determines whether an interval pattern during the first arrhythmia event corresponds to a predetermined pattern, and determines whether a difference between a cycle length corresponding to sensed cardiac signals during the first arrhythmia event prior to delivery of the first therapy and a cycle length corresponding to sensed cardiac signals during delivery of the first therapy is less than or equal to a predetermined threshold.

2. The device of claim 1, wherein the predetermined pattern corresponds to one of a 1:1 atrioventricular pattern that is supraventricular in origin, a 1:1 atrioventricular pattern that is ventricular in origin, a greater than 1:1 atrioventricular pattern that is supraventricular in origin, and a greater than 1:1 atrioventricular pattern that is simultaneous supraventricular and ventricular in origin.

3. A medical device for discriminating arrhythmia events, comprising:
   an input circuit sensing cardiac signals;
   a microprocessor identifying an event associated with the sensed cardiac signals as a first arrhythmia event;
   a first circuit delivering a first therapy;
   a second circuit for delivering a second therapy, the second circuit including an energy storage device to store energy associated with the second therapy and a charging circuit selectively coupled to the energy storage device to generate the stored energy; and
   a control circuit controlling the first circuit and the second circuit to deliver the first therapy substantially simultaneous with coupling of the charging circuit and the energy storage device in response to the first arrhythmia event, wherein the microprocessor evaluates a physiologic response to the delivered first therapy and determines the event is other than the first arrhythmia event in response to the evaluated physiologic response and the control circuit decouples the charging circuit and the energy storage device in response to the event being other than the first arrhythmia event, wherein the microprocessor determines whether an interval pattern during the first arrhythmia event corresponds to a predetermined pattern, and determines whether a difference between a cycle length corresponding to sensed cardiac signals during the first arrhythmia event prior to delivery of the first therapy and a cycle length corresponding to sensed cardiac signals during delivery of the first therapy is less than or equal to a predetermined threshold.

4. The device of claim 3, wherein the predetermined pattern corresponds to one of a 1:1 atrioventricular pattern that is supraventricular in origin, a 1:1 atrioventricular pattern that is ventricular in origin, a greater than 1:1 atrioventricular pattern that is supraventricular in origin, and a greater than 1:1 atrioventricular pattern that is simultaneous supraventricular and ventricular in origin.

5. A method for discriminating arrhythmia events, comprising:
   sensing cardiac signals;
   identifying an event associated with the sensed cardiac signals as a first arrhythmia event;
   delivering a first therapy, substantially simultaneous with coupling of a charging circuit and an energy storage device to generate stored energy on the energy storage device, in response to the first arrhythmia event;
   evaluating a physiologic response to the delivered first therapy; and determining the event is other than the first arrhythmia event in response to the evaluated physiologic response, wherein evaluating a physiologic response comprises:

determining whether an interval pattern during the first arrhythmia event corresponds to a predetermined pattern; and determining whether a difference between cycle length corresponding to sensed cardiac signals during the first arrhythmia event prior to delivery of the first therapy and a cycle length corresponding to sensed cardiac signals during delivery of the first therapy is less than or equal to a predetermined threshold.

6. The method of claim 5, wherein the predetermined pattern corresponds to one of a 1:1 atrioventricular pattern that is supraventricular in origin, a 1:1 atrioventricular pattern that is ventricular in origin, a greater than 1:1 atrioventricular pattern that is supraventricular in origin, and a greater than 1:1 atrioventricular pattern that is simultaneous supraventricular and ventricular in origin.

7. A computer readable medium having computer executable instructions for performing a method comprising:

sensing cardiac signals;

identifying an event associated with the sensed cardiac signals as a first arrhythmia event;

delivering a first therapy, substantially simultaneous with coupling of a charging circuit and an energy storage device to generate stored energy on the energy storage device, in response to the first arrhythmia event;

evaluating a physiologic response to the delivered first therapy; and determining the event is other than the first arrhythmia event in response to the evaluated physiologic response, wherein evaluating a physiologic response comprises:

determining whether an interval pattern during the first arrhythmia event corresponds to a predetermined pattern; and determining whether a difference between cycle length corresponding to sensed cardiac signals during the first arrhythmia event prior to delivery of the first therapy and a cycle length corresponding to sensed cardiac signals during delivery of the first therapy is less than or equal to a predetermined threshold.

8. A medical device system for discriminating arrhythmia events, comprising:

means for sensing cardiac signals;

means for identifying an event associated with the sensed cardiac signals as a first arrhythmia event;

means for delivering a first therapy, substantially simultaneous with coupling of a charging circuit and an enemy storage device to generate stored energy on the energy storage device, in response to the first arrhythmia event;

means for evaluating a physiologic response to the delivered first therapy; and means for determining the event is other than the first arrhythmia event in response to the evaluated physiologic response, wherein means for evaluating a physiologic response comprises:

means for determining whether an interval pattern during the first arrhythmia event corresponds to a predetermined pattern; and means for determining whether a difference between cycle length corresponding to sensed cardiac signals during the first arrhythmia event prior to delivery of the first therapy and a cycle length corresponding to sensed cardiac signals during delivery of the first therapy is less than or equal to a predetermined threshold.

9. The medical device system of claim 8, wherein the predetermined pattern corresponds to one of a 1:1 atrioventricular pattern that is supraventricular in origin, a 1:1 atrioventricular pattern that is ventricular in origin, a greater than 1:1 atrioventricular pattern that is supraventricular in origin, and a greater than 1:1 atrioventricular pattern that is simultaneous supraventricular and ventricular in origin.

* * * * *

UNITED STATES PATENT AND TRADEMARK OFFICE
CERTIFICATE OF CORRECTION

| | |
|---|---|
| PATENT NO. | : 7,317,942 B2 |
| APPLICATION NO. | : 10/839634 |
| DATED | : January 8, 2008 |
| INVENTOR(S) | : Mark L. Brown |

It is certified that error appears in the above-identified patent and that said Letters Patent is hereby corrected as shown below:

Col. 16, line 13, delete "enemy storage" and insert in place there of --energy storage--.

Signed and Sealed this

Sixth Day of January, 2009

JON W. DUDAS
*Director of the United States Patent and Trademark Office*